United States Patent [19]

Ransley

[11] 4,046,824
[45] Sept. 6, 1977

[54] PROCESS FOR SELECTIVE HYDROGENATION OF ETHYLBENZENE

[75] Inventor: Derek L. Ransley, Berkeley, Calif.

[73] Assignee: Chevron Research Company, San Francisco, Calif.

[21] Appl. No.: 645,586

[22] Filed: Dec. 31, 1975

[51] Int. Cl.$^2$ .......................... C07C 5/10; C07C 5/14
[52] U.S. Cl. ............................. 260/667; 260/666 P; 260/674 A
[58] Field of Search ............... 260/674 A, 667, 666 P

[56] References Cited

U.S. PATENT DOCUMENTS

| 2,282,231 | 5/1942 | Mattox | 260/674 A |
| 3,183,278 | 5/1965 | Koch | 260/667 |
| 3,432,565 | 3/1969 | Kouwenkoven et al. | 260/667 |
| 3,868,430 | 2/1975 | Giangaspero et al. | 260/674 A |
| 3,956,103 | 5/1976 | Antos | 208/139 |

Primary Examiner—Veronica O'Keefe
Attorney, Agent, or Firm—D. A. Newell; John Stoner, Jr.; W. Keith Turner

[57] ABSTRACT

An improved process for selective hydrogenation of ethylbenzene which employs a rhodium catalyst and mild reaction conditions, and is especially useful to reduce the concentration of ethylbenzene in mixtures comprising ethylbenzene and at least one xylene isomer.

14 Claims, No Drawings

PROCESS FOR SELECTIVE HYDROGENATION OF ETHYLBENZENE

BACKGROUND OF THE INVENTION

Para-xylene is in demand as a precursor in the production of terephthalic acid and dimethyl terephthalate which are, in turn, used in the manufacture of polyester resins. Mixtures containing substantial guantities of ethylbenzene and xylene isomers are prepared by catalytic reforming of petroleum fractions and catalytic isomerization of xylenes. Typical processes for separating p-xylene from $C_8$ aromatic mixtures involve fractional crystallization. In order to provide an improved feedstock for para-xylene crystallization processes it is desirable to reduce the concentration of ethylbenzene in the aromatic mixture. Ethylbenzene acts as a diluent in crystallization minimizing the production of p-xylene from a given size crystallization apparatus and lowering the eutectic temperature of the mixtue which, if obtained, results in a higher viscosity slurry and a lower density difference between the p-xylene crystals and the mother liquor. Thus, the presence of ethylbenzene impedes the separation of p-xylene crystals.

It is known that the boiling points of the $C_8$ aromatics are very close. In particular, ethylbenzene boils at about 136° C, p-xylene at about 138° C, m-xylene at about 139° C, and o-xylene at about 144° C. While ethylbenzene can be separated from xylene isomers by fractional distillation, typical ethylbenzene fractionators contain 300 to 400 actual trays and require about a 25–50 to 1 feed ratio.

Accordingly, there is a continuing need to provide a process for reducing the concentration of ethylbenzene in $C_8$ aromatic mixtures, thereby providing a more efficient less expensive p-xylene crystallization feedstock. One approach to the separation of ethylbenzene and xylenes has been to hydrogenate the $C_8$ mixture prior to separation. Interest in this approach stems from the greater difference in boiling points between ethylcyclohexane and the dimethyl cyclohexanes than between ethylbenzene and the xylenes. U.S. Pat. No. 2,282,231 describes such a process. While complete hydrogenation of the $C_8$ mixture is satisfactory, it suffers certain shortcomings. For example, it is suggested that the feedstock should not contain o-xylene. This, the $C_8$ mixture should first be distilled to separate the o-xylene fraction. It is also necessary to reform the resulting substituted cyclohexanes to xylenes in order to obtain the desired p-xylene-containing mixture. Thus, an additional step is required. These shortcomings could be overcome by providing a hydrogenation process which selectively hydrogenates ethylbenzene in a $C_8$ aromatic mixture.

SUMMARY OF THE INVENTION

It has now been found that ethylbenzene in a $C_8$ aromatic mixture is preferentially hydrogenated by heating the mixture in the presence of a rhodium catalyst at a temperature within the range of from about 20° C to 90° C and a hydrogen pressure of from about 0.5 atmosphere to 15 atmospheres.

DETAILED DESCRIPTION OF THE INVENTION

The process of this invention relates to the discovery that, by employing a catalysyt consisting essentially of rhodium, ethylbenzene can be selectively hydrogenated under unusually mild hydrogenation conditions. This discovery can be advantageously employed in a process for separating ethylbenzene and xylenes.

At equilibrium typical $C_8$ aromatic mixtures will have concentrations of ethylbenzene and the xylene isomers as shown in the following table.

TABLE 1

EQUILIBRIUM $C_a$ AROMATIC COMPOSITIONS

| Temperature, ° C | 327 | 427 | 527 |
|---|---|---|---|
| Mol percent of isomers | | | |
| Ethylbenzene | 6 | 8 | 11 |
| Para-xylene | 22 | 22 | 21 |
| Meta-xylene | 50 | 48 | 45 |
| Orthc-xylene | 22 | 22 | 23 |

In actual practice, the feed mixtures of the $C_8$ aromatics employed by the process of this invention will typically have approximately equal concentrations of ethylbenzene and each of the xylene isomers. In addition, typical feed mixtures may contain small quantities of higher molecular weight aromatics as well as nonaromatic hydrocarbons such as straight- or branched-chain paraffins, cycloparaffins, or olefinics.

In accordance with the process of this invention, a mixture of $C_8$ aromatic hydrocarbons comprising ethylbenzene is heated in the presence of a catalyst consisting essentially of rhodium at a temperature from about 20° C to about 90° C, preferably from about 30° C to about 60° C, and a hydrogen pressure from about 0.5 atmosphere to about 15 atmospheres, preferably from about 0.5 atmosphere to about 5 atmospheres.

It has been found that the selection of a rhodium catalyst is critical. U.S. Pat. No. 3,868,430 describes catalytic hydrogenation of ethylbenzene and emphasizes that the best possible selectivity is obtained using mild reaction conditions. Rhodium catalysts have been found to promote the preferential hydrogenation of ethylbenzene under unexpectedly mild reaction conditions, in particular at unusually low temperatures.

Rhodium catalysts suitable for use in the process of this invention, while preferably consisting essentially of rhodium, may comprise non-interferring amounts of other transition metals such as palladium or platinum. Supported rhodium catalysts are especially effective for use herein. Typical supported catalysts comprise from about 0.5% to about 10%, by weight, of rhodium on a high surface area support such as powdered alumina or activated charcoal. Other catalytic supports such as aluminum oxide and carbon are also effective carriers for the rhodium catalyst. These and other rhodium catalysts are commercially available. While the amount of catalyst employed may vary over a wide range, depending upon the particular rhodium catalyst employed, reaction conditions and the like, for general guidance liquid hourly space velocities range from about 0.5 to about 5.0. As a rule, space velocities outside this range do not provide significantly improved conversions or selectivities.

The hydrogenation of ethylbenzene, catalyzed by rhodium, is carried out in the fluid phase according to conventional methods under unexpectedly mild conditions. Satisfactory temperatures range from about 20° C to about 90° C, preferably from about 40° C to about 60° C. Satisfactory pressures range from about 0.5 atmosphere to about 15 atmospheres, preferably from about 0.5 atmosphere to about 5 atmospheres. Satisfactory hydrogen-to-hydrocarbon ratios vary from about 0.1:1 to about 10:1. Liquid hourly space velocities of the hydrocarbon charge of from about 0.5 to about 5.0 volumes per volume of catalyst per hour are satisfactory, preferably from about 0.7 hour$^{-1}$ to about 3.0 a 0.5 inch-diameter reactor equipped with pressure and heating means. The following table summarizes the results of typical runs.

TABLE II

| | | CONDITIONS AND RESULTS OF HYDROGENATION WITH 0.5% RHODIUM ON ALUMINA CATALYST | | | | | | | | |
|---|---|---|---|---|---|---|---|---|---|---|
| | | EXAMPLES | | | | | | | | |
| | Feed | 1 | 2 | 3 | 4 | 5 | 6 | 7 | 8 | 9 |
| Temperature, °f | | 140 | 100 | 120 | 120 | 140 | 100 | 120 | 130 | 140 |
| Pressure, psig. | | 45 | 40 | 40 | 45 | 45 | 55 | 55 | 50 | 50 |
| H$_2$/HC | | 10 | 10 | 10 | 10 | 10 | 10 | 10 | 10 | 10 |
| LHSV | | 1.5 | 0.7 | 0.7 | 1.5 | 1.5 | 3.0 | 3.0 | 3.0 | 2.4 |
| Composition, Wt% | | | | | | | | | | |
| Toluene) Non-Aromatics) | 19.6 | 35.6 | 34.5 | 40.0 | 25.5 | 32.6 | 23.1 | 23.7 | 26.4 | 27.8 |
| Ethylbenzene | 11.1 | 4.3 | 5.1 | 3.1 | 6.3 | 4.7 | 9.2 | 8.4 | 7.6 | 7.1 |
| Paraxylene | 12.5 | 10.7 | 11.1 | 10.3 | 11.6 | 10.9 | 12.4 | 12.0 | 11.8 | 11.6 |
| Metaxylene | 28.6 | 24.6 | 25.4 | 23.9 | 26.5 | 25.3 | 28.2 | 27.6 | 27.0 | 26.7 |
| Orthoxylene | 14.7 | 12.5 | 12.4 | 11.5 | 13.5 | 13.1 | 14.5 | 14.2 | 13.8 | 13.6 |
| C$_9$+ | 13.3 | 12.4 | 11.6 | 11.7 | 12.5 | 13.4 | 12.7 | 14.1 | 13.4 | 13.2 |
| Total Xylenes | 55.9 | 47.7 | 48.8 | 45.6 | 51.7 | 49.3 | 55.0 | 53.8 | 52.6 | 51.9 |
| Conversion % | | | | | | | | | | |
| Total C$_8$ | | 16.0 | 14.9 | 20.0 | 5.9 | 13.0 | 3.7 | 4.1 | 6.8 | 8.2 |
| Ethylbenzene | | 61.3 | 54.1 | 72.5 | 42.9 | 57.6 | 16.7 | 24.0 | 31.8 | 36.0 |
| Paraxylene | | 14.4 | 11.2 | 17.6 | 7.2 | 12.8 | 0.8 | 4.0 | 5.6 | 7.2 |
| Metaxylene | | 14.0 | 11.2 | 16.4 | 7.3 | 11.5 | 1.4 | 3.5 | 5.6 | 6.6 |
| Orthoxylene | | 14.9 | 15.6 | 21.8 | 7.9 | 10.8 | 1.4 | 3.4 | 6.1 | 7.5 |
| Total Xylenes | | 14.7 | 12.6 | 18.4 | 7.7 | 11.8 | | 3.7 | 5.9 | 7.2 |
| Selectivity | | 4.2 | 4.3 | 3.9 | 5.6 | 4.9 | 10.4 | 6.7 | 5.4 | 5.0 | hour$^{-1}$. Under these conditions ethylbenzene is preferentially hydrogenated at selectivities of from about 2 to about 10 mols of ethylbenzene hydrogenated per mol of xylene hydrogenated. Particularly good selectivity is obtained at a temperature of about 40° C, a pressure of about 5 atmospheres, a hydrogen-to-hydrocarbon ratio of about 10:1 and a liquid hourly space velocity of about 3.0.

It has been found that selectivity decreases with increasing conversions. For example, selectivities of from about 5:1 to about 2:1 are obtained at aromatic conversions of from about 10% to about 20%. Conversions as used herein refer to the mols of aromatic feed stock hydrogenated expressed as percent based on the total aromatic content of feedstock. Selectivities of from about 10:1 to about 5:1 are obtained at conversions in the range of from about 5% to about 10%. In a preferred embodiment of this invention the selective hydrogenation of a C$_8$ aromatic mixture is effected at a total aromatic conversion of about 5%, preferably about 10% to about 30%. Acceptable conversions may range as high as 50% to 60%. At these conversions the selectivity of the hydrogenation is adequate to effect an efficient and economic separation of ethylbenzene as ethylcyclohexane.

After selective hydrogenation of the C$_8$ aromatic mixture, the partially reduced product is separated into an aromatic fraction and a non-aromatic fraction. Separation may be effected by distillation or extraction. The aromatic fraction comprises the non-hydrogenated xylenes and some ethylbenzene, the non-aromatic fraction comprises ethylcyclohexane and some naphthenes. The ethylbenzene reduced aromatic fraction is a preferred feedstock to a p-xylene crystallization process or crystallization/isomerization process.

The following examples further illustrate the practice of this invention.

EXAMPLES 1-9

In the following examples, the reactions were run in the liquid phase with 10 to 27 ml of a 0.5% rhodium catalyst on an alumina support. Samples were analyzed by gas phase chromatography using a 100 feet by 0.02 inch coated column at 70° C. The reactions were run in

What is claimed is:

1. A process for selectively hydrogenating ethylbenzene in a C$_8$ aromatic mixture comprising ethylbenzene and at least one xylene isomer, which comprises heating said mixture with hydrogen in the presence of a catalyst consisting essentially of rhodium until from about 5% to about 60% of said mixture is hydrogenated.

2. A process according to claim 1 wherein said heating is carried out at a temperature in the range of from about 20° C to about 90° C.

3. A process according to claim 2 wherein said heating is carried out at a hydrogen pressure of from about 0.5 atmospheres to about 15 atmospheres.

4. A process according to claim 1 wherein said C$_8$ aromatic mixture comprises approximately equal amounts of ethylbenzene, p-xylene, o-xylene, and meta-xylene.

5. A process according to claim 1 wherein said rhodium catalyst is supported on an alumina.

6. A process according to claim 1 wherein said process is carried out at an aromatic conversion of from about 10% to about 30%.

7. A process according to claim 1 wherein said process is carried out at an aromatic conversion of from about 5% to about 10%.

8. An improved process for preparing a ethylbenzene reduced C$_8$ aromatic mixture which comprises heating a C$_8$ aromatic feed mixture comprising ethylbenzene and at least one xylene isomer with hydrogen in the presence of a rhodium catalyst until from about 5% to about 60% of the feed mixture is hydrogenated, and separating the hydrogenated non-aromatic fraction comprising ethylcyclohexane.

9. A process according to claim 8 wherein said conditions include a temperature of from about 20° C to about 90° C.

10. A process according to claim 8 wherein said rhodium catalyst is supported on alumina.

11. A process according to claim 8 wherein said process is carried out at a aromatic conversion of from about 10% to about 30%.

12. A process according to claim 8 wherein said separation is effected by distillation.

13. A process according to claim 1 wherein said heating is carried out at a temperature of from about 30° C to about 60° C.

14. A process according to claim 1 wherein said process is carried out in the fluid phase at a temperature of about 40° C, a hydrogen pressure of about 5 atmospheres, a hydrogen-to-hydrocarbon ratio of about 10:1, and a liquid hourly space velocity of hydrocarbon charge of about 3.0 volumes per volume of catalyst per hour.

* * * * *